(12) United States Patent
Plückthun et al.

(10) Patent No.: US 6,630,317 B1
(45) Date of Patent: Oct. 7, 2003

(54) METHODS FOR OBTAINING, IDENTIFYING AND APPLYING NUCLEIC ACID SEQUENCES AND (POLY)PEPTIDES WHICH INCREASE THE EXPRESSION YIELDS OF PERIPLASMIC PROTEINS IN FUNCTIONAL FORM

(75) Inventors: Andreas Plückthun, Zürich (CH); Hendrick Bothmann, Zürich (CH)

(73) Assignee: University of Zurich, Zurich (CH)

( * ) Notice: Subject to any disclaimer, the term of this patent is extended or adjusted under 35 U.S.C. 154(b) by 0 days.

(21) Appl. No.: 09/564,351

(22) Filed: May 1, 2000

Related U.S. Application Data

(63) Continuation of application No. PCT/EP98/06755, filed on Oct. 23, 1998.

(30) Foreign Application Priority Data

Oct. 23, 1997 (EP) ............................. 97118457

(51) Int. Cl.[7] ........................ G01N 33/573; G01N 33/53
(52) U.S. Cl. .................. 435/7.4; 435/7.1; 435/DIG. 8; 435/DIG. 15; 435/DIG. 17; 935/11; 935/38; 935/49
(58) Field of Search ........................... 435/7.1, 6.9, 7.4, 435/DIG. 8, DIG. 15, DIG. 17; 935/11, 38, 49

(56) References Cited

U.S. PATENT DOCUMENTS 5,246,838 A * 9/1993 Van Dijl et al. ........... 435/69.1

OTHER PUBLICATIONS

Missiakas et al. Molecular Microbiology 21(4):871–884 (1996).*
Wall et al. Current Opinion in Biotechnology 6:507–516 (1995).*
Aasland, R. et al., "Identity of the 17–Kilodalton Protein, a DNA–Binding Protein from *Escherichia coli*, and the firA Gene Product," *Journal of Bacteriology*, 170, 5916–5918 (1988).
Bardwell, J. C. A. et al., "Building Bridges: Disulphide Bond Formation in the Cell," *Molecular Microbiology*, 14, 199–205 (1994).
Bothmann, H. et al., "Selection for a Periplasmic Factor Improving Phage Display and Functional Periplasmic Expression," *Nature Biotechnology*, 16, 376–380 (1998).
Buchner, J., "Supervising the Fold: Functional Principles of Molecular Chaperones," 10, 10–19 (1996).
Chen, R. et al., "A Periplasmic Protein (Skp) of *Escherichia coli* Selectively Binds a Class of Outer Membrane Proteins," *Molecular Microbiology*, 19, 1287–1294 (1996).
Delamarche, C. et al., "Characterization of the *Pasteurella multocida skp* and fir A Genes," *Gene*, 161, 39–43 (1995).

Dunn, I. S., "Phage Display of Proteins," *Current Opinion Biotechnololgy*, 7, 547–553 (1996).
Fleischmann, R. D. et al., "Whole–Genome Random Sequencing and Assembly of *Haemophilus influenzae* Rd," *Science*, 269, 496–512 (1995).
Geyer, R. et al., "A Lipopolysaccharide–Binding Cell–Surface Protein from *Salmonella minnesota*. Isolation, Partial Characterization and Occurrence in Different Enterobacteriaceae," *Eur. J. Biochem.*, 98, 27–38 (1979).
Gill, S. C. et al., "Calculation of Protein Extinction Coefficients from Amino Acid Sequence Data ," Analytical Biochemistry, 182, 319–326 (1989).
Hirvas, L. et al., "Bacterial 'Histone–Like Protein I' (HLP–I) is an Outer Membrane Constituent?," *FEBS Lett.*, 262, 123–126 (1990).
Hirvas, L. et al., "The ompH Gene of *Yersinia enterocolitica*: Cloning, Sequencing, Expression, and Comparison with Known Enterobacterial ompH Sequences," *Journal of Bacteriology*, 173, 1223–1229 (1991).
Holck. A, et al., "Cloning and Sequencing of the Gene for the DNA–binding 17K Protein of *Escherichia coli*," *Gene*, 67, 117–124 (1988).
Hottenrott, S. et al., "The *Escherichia coli* SlyD Is a Metal Ion–regulated Peptidyl–prolyl cis/trans–Isomerase," *The Journal of Biological Chemistry*, 272, 15697–15701 (1997).
Jung, S. et al., "Improving in vivo Folding and Stability of a Single–Chain Fv Antibody Fragment by Loop Grafting," *Protein Engineering*, 10, 959–966 (1997).
Knappik, A. et al., "The Effect of Folding Catalysts on the In Vitro Folding Process of Different Antibody Fragments Expressed in *Escherichia Coli*," *Bio. Technology*, 11, 77–83 (1993).
Knappik, A. et al., "Engineered Turns of a Recombinant Antibody Improve its in vivo Folding," *Protein Engineering*, 8, 81–89, (1995).
Koski, P. et al., "Complete Sequence of the ompH Gene Encoding the 16–kDa Cationic Outer Membrane Protein of *Salmonella typhimurium*," *Gene*, 88, 117–120 (1990).
Koski, P. et al., "Isolation, Cloning, and Primary Structure of a Cationic 16–kDa Outer Membrane Protein of *Salmonella typhimurium*," *The Journal of Biological Chemistry*, 264, 18973–18980 (1989).

(List continued on next page.)

*Primary Examiner*—Andrew Wang
*Assistant Examiner*—Tomas Friend
(74) *Attorney, Agent, or Firm*—Heller Ehrman White and McAuliffe

(57) ABSTRACT

The present invention relates to a method for obtaining nucleic acid sequences encoding (poly)peptides which increase the expression yields of periplasmic proteins in functional form upon co-expression of said (poly)peptides and said periplasmic proteins. The invention also provides a method for the identification of said (poly)peptides. Furthermore, the present invention relates to a method for increasing the expression yields of periplasmic proteins in functional form by co-expressing (poly)peptides, for example Skp, FkpA, or a homolog of Skp or FkpA, in bacteria.

12 Claims, 10 Drawing Sheets

OTHER PUBLICATIONS

Krebber, A. et al., "Reliable Cloning of Functional Antibody Variable Domains from Hybridomas and Spleen Cell Repertoires Employing a Reengineered Phage Display System," *Journal of Immunological Methods*, 201, 35–55 (1997).

Krebber, C. et al., "Selectively–Infective Phage (SIP): A Mechanistic Dissection of a Novel in vivo Selection for Protein–Ligand Interactions," *J. Mol. Biol.*, 268, 607–618 (1997).

Martin, J. et al., "Chaperone–Assisted Protein Folding," *Current Opinion in Structural Biology*, 7, 41–52 (1997).

Missiakas, D. et al., "Protein Misfolding in the Cell Envelope of *Escherichia coli*: New Signaling Pathways," *Trends Biochem Sci.*, 22, 59–63 (1997).

Missiakas, D. et al., "New Components of Protein Folding in Extracytoplasmic Compartments of *Escherichia coli*, Sur A, FkpA and Skp/OmpH," *Molecular Microbiology*, 21, 871–884 (1996).

Nieba, L. et al., "BIACORE Analysis of Histidine–Tagged Proteins Using a Chelating NTA Sensor Chip," *Analytical Biochemistry*, 252, 217–228 (1997).

Proba, K. et al., "A Natural Antibody Missing a Cysteine in $V_H$: Consequences for Thermodynamic Stability and Folding," J. Mol. Biol., 265, 161–172 (1997).

Proba, K. et al., "Antibody scFv Fragments Without Disulfide Bonds Made by Molecular Evolution," *J. Mol. Biol.*, 275, 245–253 (1998).

Roof, W.D. et al., "slyD, a Host Gene Required for ΦX174 Lysis, Is Related to the FK506–binding Protein Family of Peptidyl–prolyl cis–trans–Isomerases," *The Journal of Biological Chemistry*, 269, 2902–2910 (1994).

Roof, W.D. et al., "Mutational Analysis of slyD, an *Escherichia coli* Gene Encoding a Protein of the FKBP Immunophilin Family," *Molecular Microbiology*, 25, 1031–1046 (1997).

Skerra, A. et al., "Assembly of a Functional Immunoglobulin $F_v$ Fragment in *Escherichia coli*," *Science*, 240, 1038–1041 (1988).

Smith, G.P., et al., "Libraries of Peptides and Proteins Displayed on Filamentous Phage," *Methods in Enzymology*, 217, 228–257 (1993).

Söderlind, E. et al., "Chaperonin Assisted Phage Display of Antibody Fragments on Filamentous Bacteriophages," *Bio/Technology*, 11, 503–506 (1993).

Szabo, A. et al., "The ATP Hydrolysis–Dependent Reaction Cycle of the *Escherichia coli* Hsp70 System–DnaK, DnaJ, and GrpE," *Proc. Natl. Acad. Sci. U.S.A.*, 91, 10345–10349 (1994).

Thome, B.M. et al., "Skp is a Periplasmic *Escherichia coli* Protein Requiring SecA and SecY for Export," *Molecular Microbiology*, 5, 2815–2821 (1991).

Thome, B.M. et al., "A Protein with Sequence Identity to Skp (FirA) Supports Protein Translocation Into Plasma Membrane Vesicles of *Escherichia coli*," *FEBS Lett.*, 269, 113–116 (1990).

Vaughan, T.J. et al., "Human Antibodies with Sub–nanomolar Affinites Isolated from a Large Non–Immunized Phage Display Library," *Nature Biotechnology*, 14, 309–314 (1996).

Virnekäs, B. et al., "Trinucleotide Phosphoramidites: Ideal Reagents for the Synthesis of Mixed Oligonucleotides for Random Mutagenesis," *Nucleic Acids Research*, 22, 5600–5607 (1994).

Wall, J.G. et al., "Effects of Overexpressing Folding Modulators on the in vivo Folding of Heterologous Proteins in *Eschichia coli*," *Current Opinion in Biotechnology*, 6, 507–516 (1995).

Whitlow, M. et al., "1.85 Å Structure of Anti–Fluorescein 4–4–20 Fab," *Protein Engineering*, 8, 749–761 (1995).

* cited by examiner

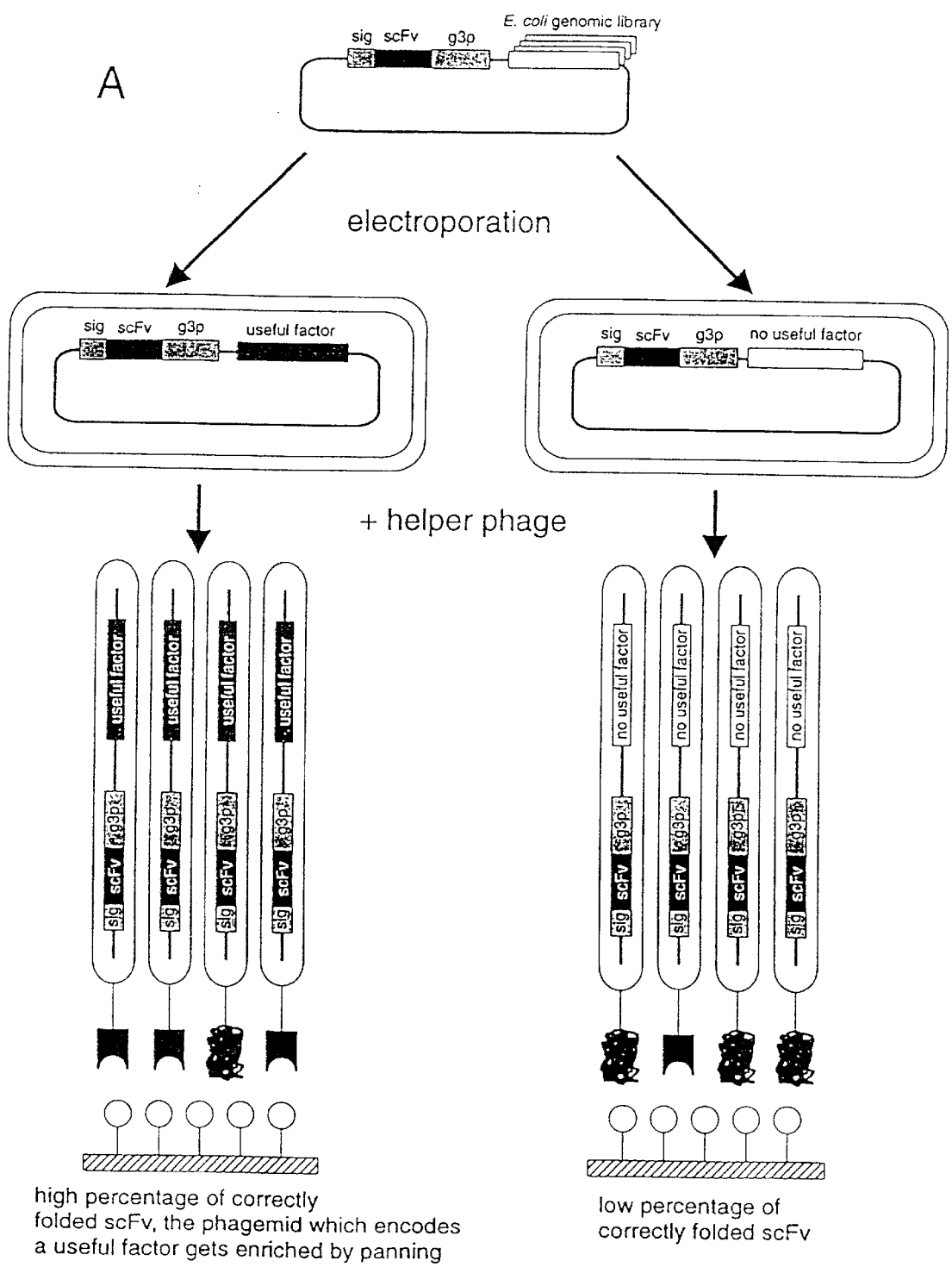
Figure 1A: Selection scheme. A. Principle of selection

Figure 1B: Selection scheme. B. Phagemid vector used for library construction
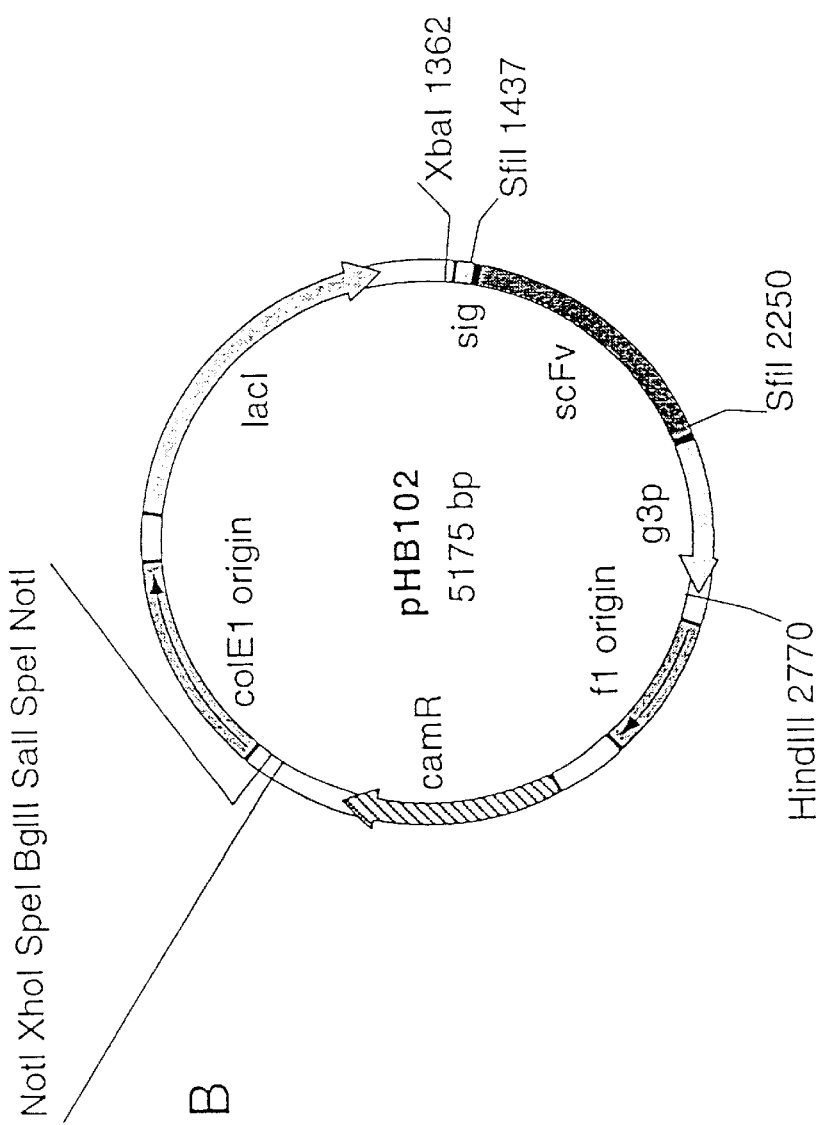

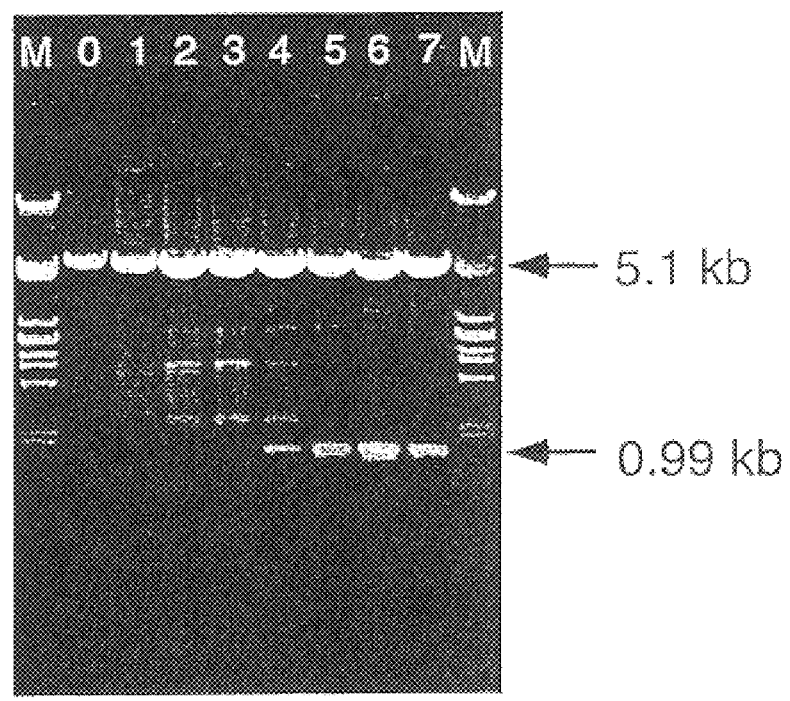
Figure 2: Analysis of phagemid pools

Figure 3: Schematic representation of the 952 bp insert
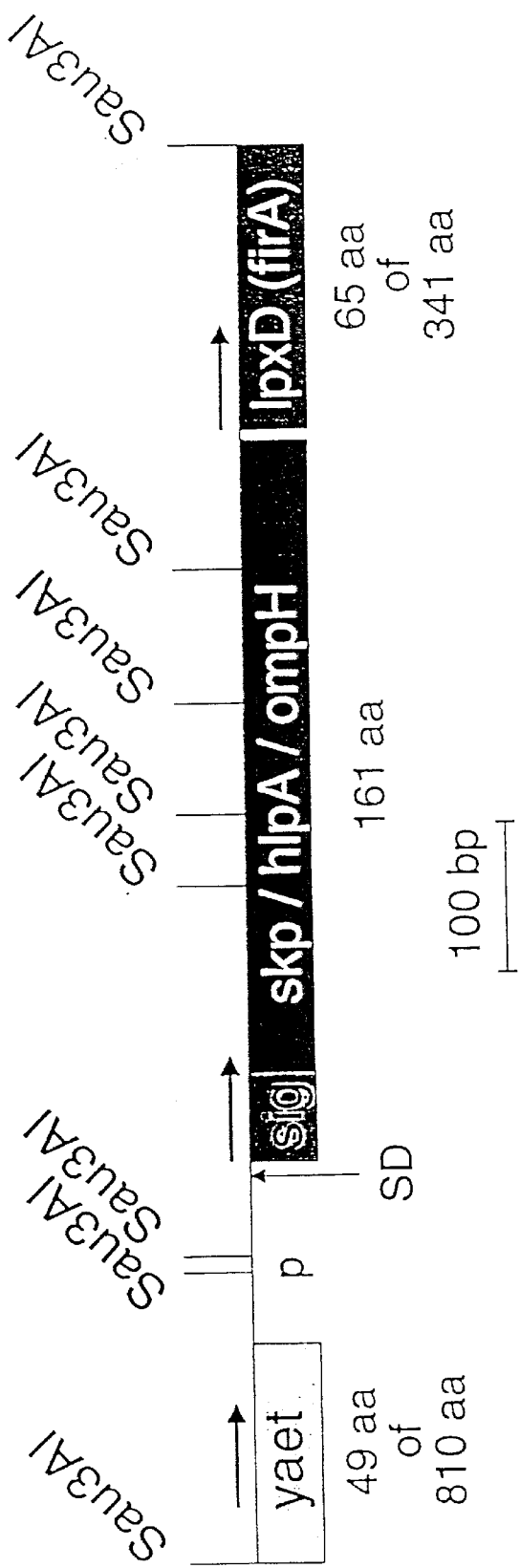

Figure 4: Antigen-binding ELISAs of phages
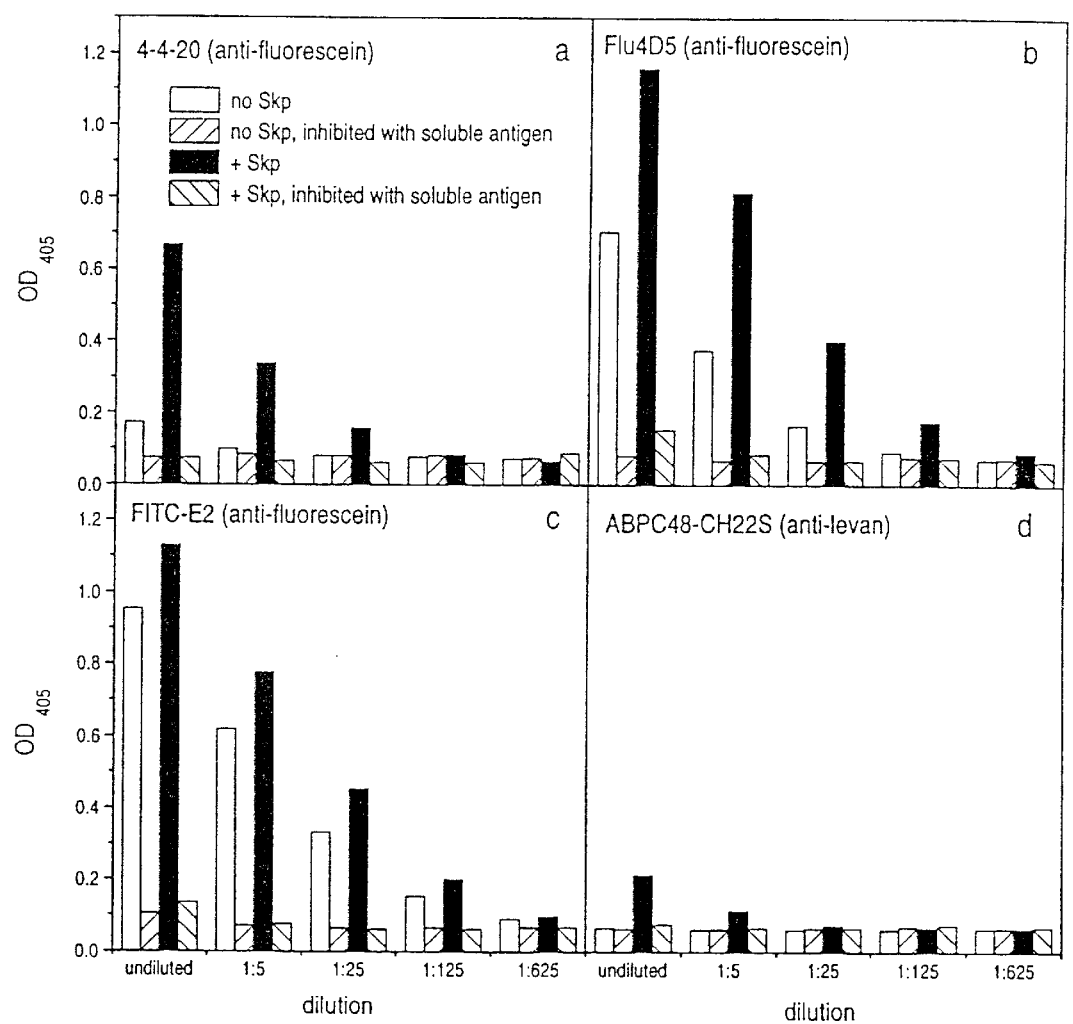

Figure 5: Phage blot
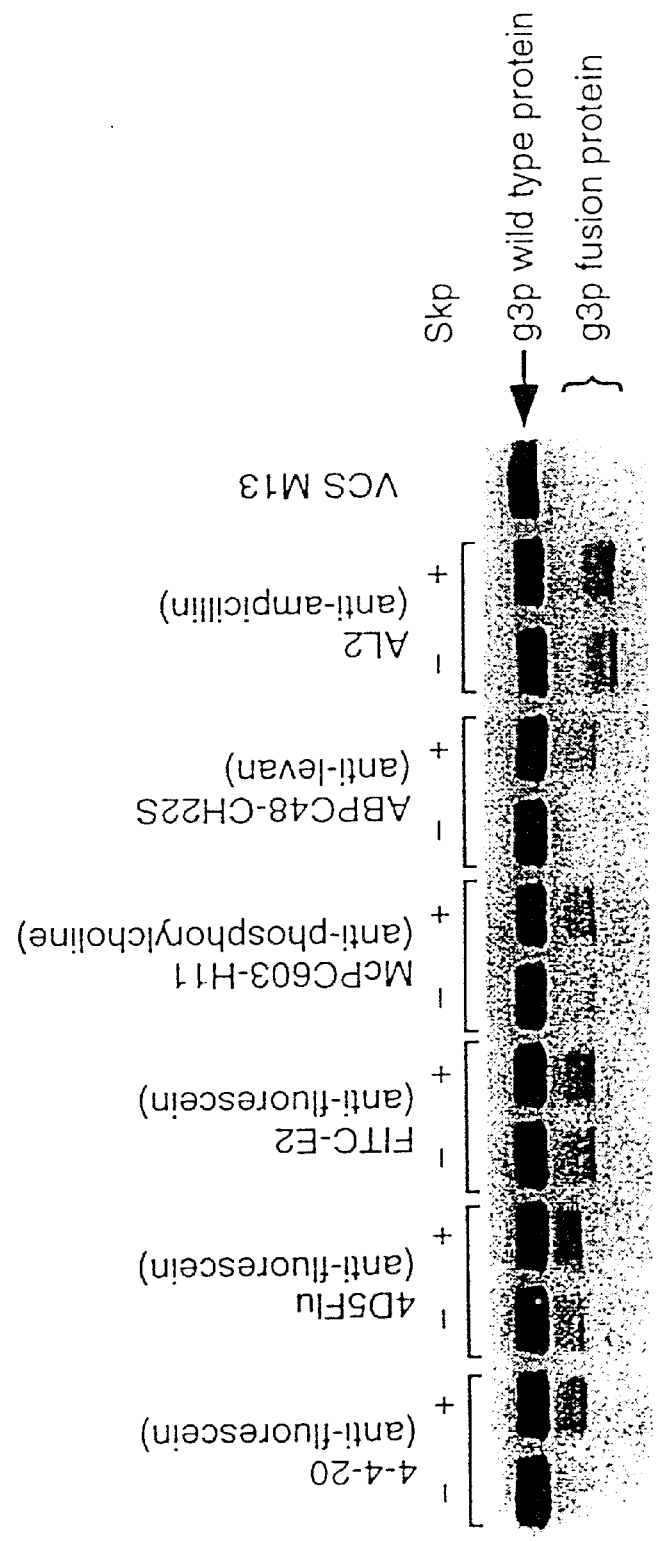

Figure 6: Crude extract ELISA
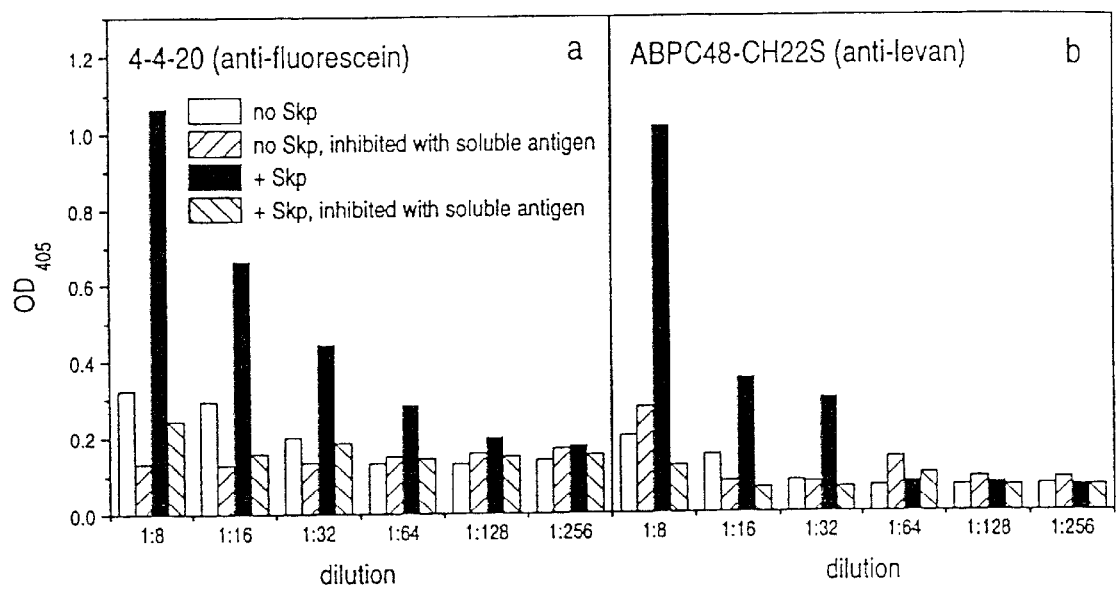

Figure 7: Analysis of phagemid pools
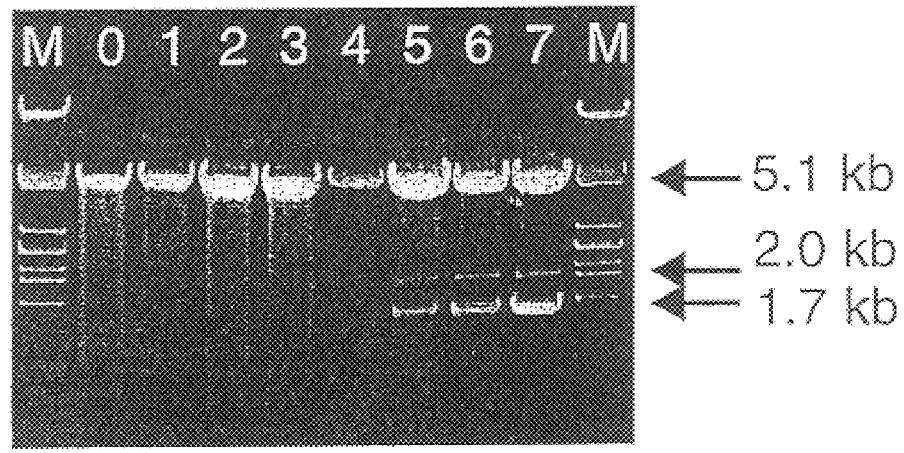

Figure 8: Schematic representations of the 1629 bp and 1987 inserts
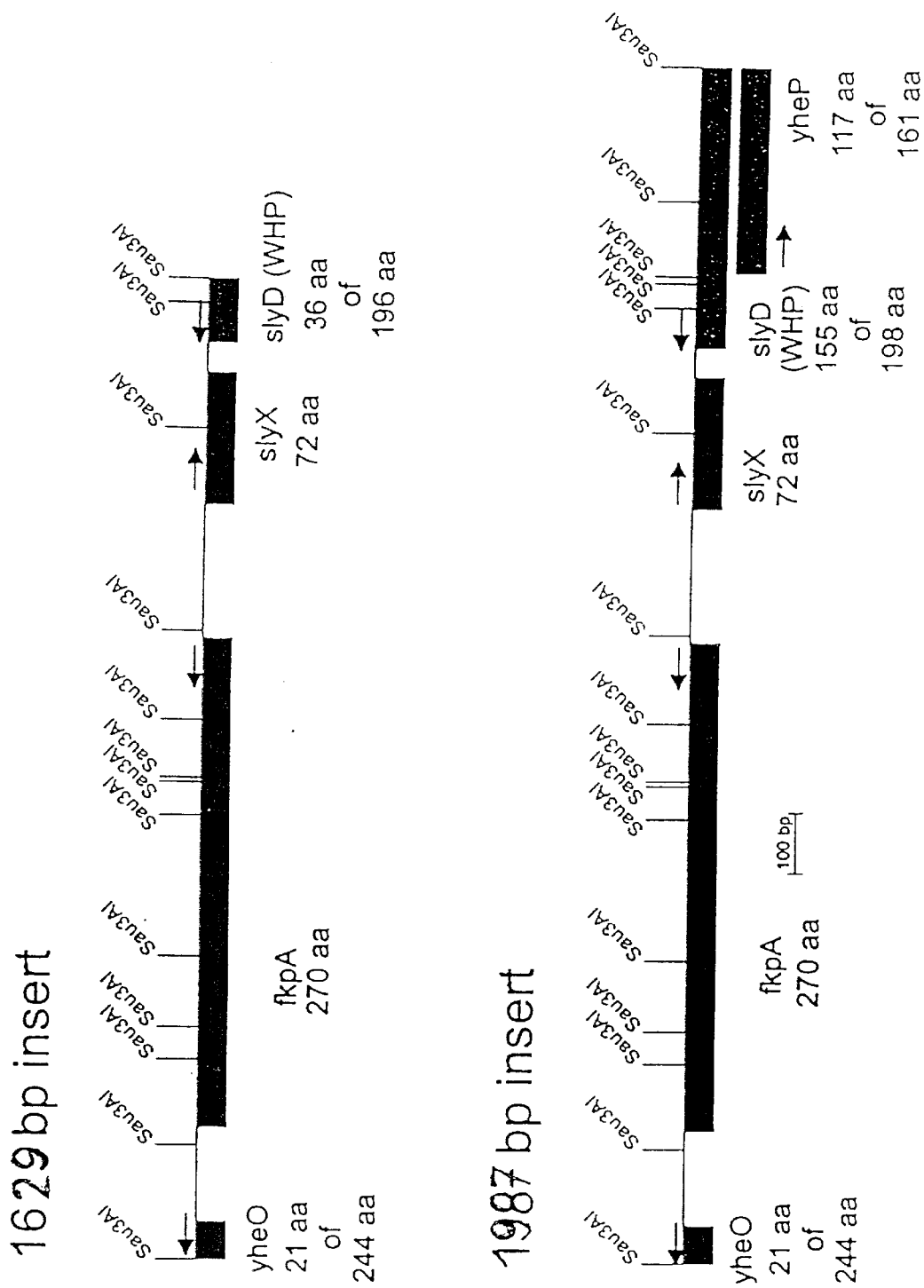

Figure 9: Antigen-binding ELISAs of phages
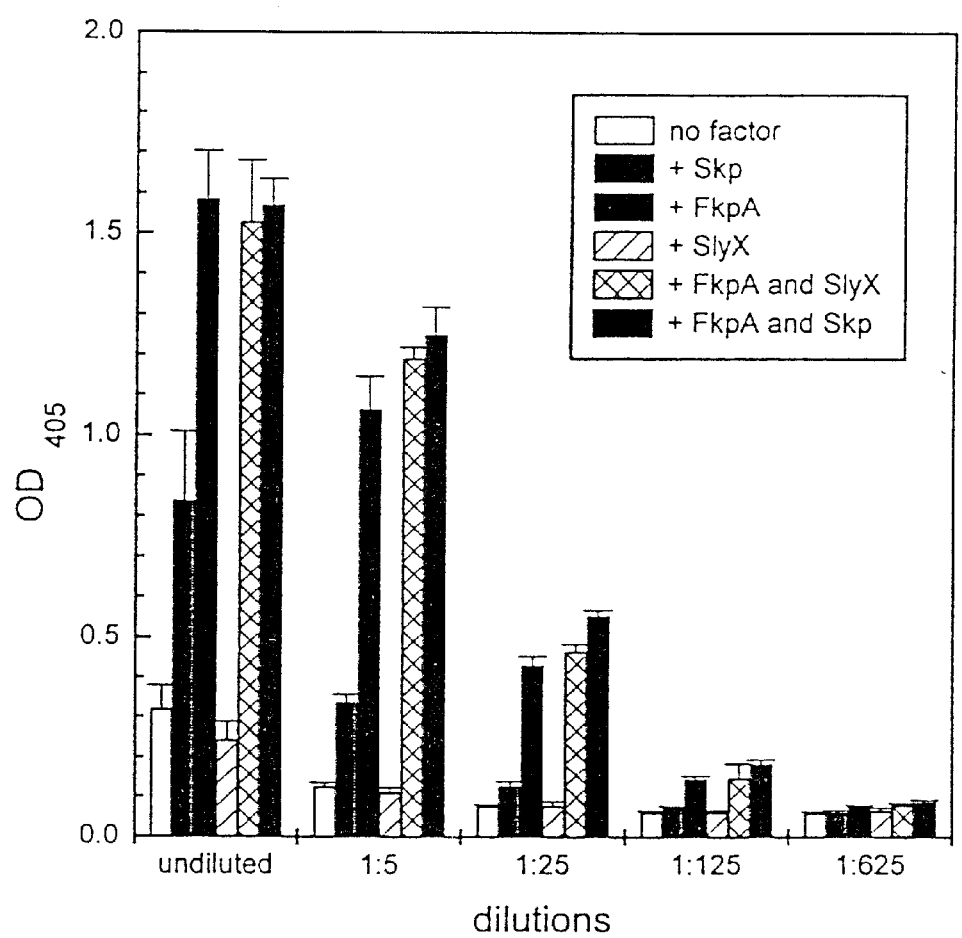

METHODS FOR OBTAINING, IDENTIFYING AND APPLYING NUCLEIC ACID SEQUENCES AND (POLY)PEPTIDES WHICH INCREASE THE EXPRESSION YIELDS OF PERIPLASMIC PROTEINS IN FUNCTIONAL FORM

CROSS REFERENCE TO RELATED APPLICATION

Under 35 U.S.C. §§120 and 365(c), this application is a continuation of copending international application PCT/EP98/06755, filed Oct. 23, 1998, designating the United States, which claims the benefit of prior European application EP 97118457.7, filed Oct. 23, 1997.

FIELD OF THE INVENTION

The present invention relates to a method for obtaining nucleic acid sequences encoding (poly)peptides which increase the expression yields of periplasmic proteins in functional form upon co-expression of said (poly)peptides and said periplasmic proteins. The invention also provides a method for the identification of said (poly)peptides. Furthermore, the present invention relates to a method for increasing the expression yields of periplasmic proteins in functional form by co-expressing (poly)peptides, for example Skp, FkpA, or a homolog of Skp or FkpA, in bacteria.

Expression in the bacterial periplasm is the most convenient route to express foreign recombinant proteins, especially proteins containing disulphides, since the bacterial disulphide forming and isomerization machinery (Bardwell, 1994) can be utilised. Nevertheless, not all proteins can be produced with high functional yield in the E. coli periplasm, and no general method for optimizing the expression in functional form of poorly folding proteins secreted into the periplasm exists.

BACKGROUND OF THE INVENTION

Another field where the correct folding of proteins in the periplasm is of crucial importance is in phage display. This method has been used over the last decade to screen libraries not only of peptides but also of a large variety of proteins (Dunn, 1996; McGregor, 1996). These displayed proteins are fused to a phage coat protein, e.g. to the N-terminus of the whole gene-3-protein (g3p) or to its C-terminal domain. These proteins therefore fold in the periplasm, while remaining anchored to the inner membrane by the C-terminal hydrophobic extension of g3p, before being incorporated into the phage coat. Therefore, the g3p fusion-proteins will almost certainly fold in the same environment and use the same machinery as periplasmically expressed proteins. Poorly folding proteins will most likely be lost over multiple screening rounds irrespective of their binding properties.

Co-expression of the cytoplasmic chaperonins GroEL and GroES during M13 phage assembly for Fab display were reported to lead to a 200fold increase in phage titer (Söderlind, 1993). However, the relative amount of functional antibody fragments being displayed by the phage particles was not affected. It was speculated that GroEL/GroES assist in phage packing and assembly, although these steps take place in the periplasm. A general method for increasing the functional display of proteins on phage is not yet available.

Consequently, there has been great interest in the question of the existence of periplasmic chaperones. However, unlike the well-characterized cytoplasmic machinery of E. coli, DnaK/DnaJ/GrpE and GroEL/GroES and possibly others (Makrides, 1996, Martin & Hartl, 1997; Buchner, 1996; EP 0 774 512 A3), the chaperone composition of the periplasm has remained poorly understood (Wall & Plückthun, 1995; Missiakas et al., 1996). While progress in elucidating the signal transduction of periplasmic stress has been made (Missiakas & Raina, 1997), the ultimate effector molecules controlling periplasmic folding have remained obscure, although some proteins, such as FkpA or SurA, were believed to act as general periplasmic folding catalysts (Missiakas et al., 1996). FkpA has first been described as very similar to the eukaryotic FK506 binding proteins (FKBPs) (Horne and Young, 1995), a class of well-characterized peptidyl-prolyl cis-trans isomerases (PPIs), which have been shown to be inhibited by the macrolipide FK506. Missiakas and co-workers showed, that the mature FkpA is located in the periplasm and assayed its activity (Missiakas et al., 1996). The estimated Kcat/Km of the cis-trans isomeration of the Ala-Pro peptidyl-prolyl bond using succinyl-Ala-Ala-Pro-Phe-4-nitroanilide (SEQ ID NO: 1) as substrate was 90mM-1s-1. FkpA is directly regulated by $\sigma^E$, which binds in its promoter region (Danese and Silhavy, 1997). The $\sigma^E$ pathway is induced by heat stress and conditions, that lead to misfolding or misassembly of outer membrane proteins (OMPs), such as over-expression of OMPs or inactivation of the surA gene.

Another protein which has been discussed in the context of periplasmic folding and protein transport is Skp. Skp is a very basic protein, which at first led to its misassignment as a DNA-binding protein (Holck et al., 1987), later as an outer membrane associated protein (Hirvas et al., 1990; Koski et al., 1990; Koski et al., 1989), and a variety of synonyms (OmpH, HlpA) witness its unclear function. Homologs have been found in Salmonella typhimurium (Koski et al., 1990; Koski et al., 1989), Yersinia enterocolitica (Hirvas et al., 1991), Yersinia pseudotuberculosis (Vuorio et al., 1991), Haemophilus influenzae (Fleischmann et al., 1995) and Pasteurella multocida (Delamarche et al., 1995). Müller and co-workers (Thome et al., 1990) showed that this protein stimulates the in vitro import of E. coli proteins into membrane vesicles and subsequently established its periplasmic location (Thome & Müller, 1991), consistent with its soluble nature and the presence of a signal sequence. More recently, it was proposed to be involved in the transport of outer membrane proteins (Chen & Henning, 1996), and when its promoter region was interrupted by a Tn10 transposon, the extreme heat shock factor $\sigma^E$ ($\sigma^{24}$) dependent response was induced (Missiakas et al., 1996). However, it remained unclear whether this is an effect of the absence of Skp or a polar effect on other proteins located downstream of skp. The heat shock response was probably induced indirectly via a change in the concentration of outer membrane proteins, which is known (Missiakas et al., 1996) to induce a $\sigma^E$ ($\sigma^{24}$).

However, attempts to increase the expression of antibody fragments in functional form by over-expressing E. coli disulphide isomerase DsbA and/or proline cis-trans isomerase PPlase A did not significantly change the folding limit (Knappik et al., 1993). It was concluded that aggregation steps in the periplasm compete with periplasmic folding, and that they may occur before disulphide formation and/or proline cis-trans isomerization take place and be independent of their extent.

In summary, no protein has up to now been identified, which unambiguously acts as a periplasmic chaperone and which could be used to optimize the expression yield of a periplasmic protein in functional form.

SUMMARY OF THE INVENTION

Thus, the technical problem underlying the present invention is to identify factors which increase the expression yield of periplasmic proteins in functional form in bacteria and to apply these factors to the optimization of expression of periplasmic proteins. The solution to the above technical problem is achieved by providing the embodiments characterized in the claims. Accordingly, the present invention allows to identify and to apply nucleic acid sequences encoding (poly)peptides which increase the expression yield of periplasmic proteins in functional form, and/or to identify and apply the (poly)peptides. The technical approach of the present invention, i.e. the co-expression of a collection of (poly)peptides with said periplasmic protein in a collection of host cells to screen or select for such nucleic acid sequences and/or (poly)peptides is neither provided nor suggested by the prior art.

Thus, the present invention relates to a method for obtaining a nucleic acid sequence comprising a (poly)peptide coding sequence, which increases the expression yield of a periplasmic protein in functional form in bacteria upon co-expression of said periplasmic protein and said (poly) peptide, comprising the steps of:

(a) providing a collection of host cells wherein each cell contains
   (i) a first nucleic acid sequence out of a collection of nucleic acid sequences, and
   (ii) a second nucleic acid sequence encoding said periplasmic protein;
(b) causing or allowing expression of
   (i) (poly)peptides expressible from said collection of nucleic acid sequences, and
   (ii) said periplasmic protein expressible from said second nucleic acid sequence;
(c) screening or selecting for a host cell expressing said periplasmic protein with increased functional yield;
(d) optionally, repeating step (c) one or more times;
(e) obtaining said first nucleic acid sequence contained in said host cell.

The term "obtaining a nucleic acid sequence" as used herein includes the at least partial identification of the nucleic acid molecule e.g. by sequencing and/or collecting the nucleic acid molecules by biochemical techniques, for example, comprised in a vector.

In the context of the present invention, the term "(poly) peptide" relates to molecules consisting of one or more chains of multiple, i.e. two or more, amino acids linked via peptide bonds. The term "protein" refers to (poly)peptides where at least part of the (poly)peptide has or is able to acquire a defined three-dimensional arrangement by forming secondary, tertiary, or quaternary structures within and/or between its (poly)peptide chain(s). This definition comprises proteins such as naturally occurring or at least partially artificial proteins, as well as fragments or domains of whole proteins, as long as these fragments or domains have a defined three-dimensional arrangement as described above. The term "periplasmic protein" relates to proteins which, after biosynthesis in the cytoplasm, are transported across the inner membrane into the periplasm. This definition comprises proteins which remain in soluble or associated form in the periplasm, which are inserted in the inner or outer membrane, which are further secreted into the medium or which are assembled into complex structures such as filamentous phages particles which are then secreted. The periplasmic proteins will normally, but not necessarily, have at least a transport signal which directs the protein to the periplasm. The term "periplasmic protein in functional form" relates to a periplasmic protein, which has a defined function, and which folds during and after expression in a way which leads to a defined three-dimensional arrangement required for the protein to be functional. A "defined function" according to the present invention is any feature of the protein which depends on the correctly folded three-dimensional arrangement, and which can be detected or determined. This comprises functions such as enzymatic activity or binding to a target or binding partner, such as in the case of receptor/ligand or antibody/antigen pairs. In addition, in the context of the present invention, said "feature" referred to hereinabove may be the presence of the correctly folded three-dimensional arrangement itself, detected or determined, for example, by an antibody recognizing the correctly assembled three-dimensional arrangement of the protein, or by measuring physico-chemical properties such as fluorescence or $\alpha$-helix content in fluorescence or CD spectra, respectively.

The term "expression yield of a periplasmic protein in functional form" relates to the amount of a periplasmic protein being produced in functional form on expression. The term "(poly)peptides expressible from said first nucleic acid sequences" relates to (poly)peptides for which open reading frames (ORFs) exist on said first nucleic acid sequences and where preferably the operator elements necessary for expression are present on the corresponding vectors comprising said nucleic acid sequences. In the case that said nucleic acid sequences comprise fragments of genomic DNA, more than one ORF may be comprised in anyone of said nucleic acid sequences. The term "functional yield" relates to the amount of said periplasmic protein being produced in functional form. Methods of designing, creating or obtaining nucleic acid sequences for expression, of constructing appropriate vectors, inserting nucleic acid sequences into vectors, choosing appropriate host cells, introducing vectors into host cells, causing or allowing expression of (poly)peptides or protein, isolating nucleic acids from host cells or identifying nucleic acid sequences and corresponding protein sequences are standard methods (Sambrook et al., 1989) which are well known to anyone of ordinary skill in the art.

In a preferred embodiment, the method of the present invention further comprises the step of identifying a (poly) peptide coding sequence comprised in said first nucleic acid sequence. The term "identifying a (poly)peptide coding sequence comprised in said first nucleic acid sequence" relates to the situation referred to hereinabove, where more than one ORF is present in said first nucleic acid sequence. When more than one ORF is found, the identifcation optionally further comprises the analysis of individual ORFs and, if necessary, further testing such as repeating steps (a) to (e) with a set of nucleic acid sequences separately representing the individual ORFs. Said further testing can be performed by anyone of ordinary skill in the art.

In a futher preferred embodiment, said periplasmic protein is not expressible, or in very low yields, in functional form when expressed under standard conditions, i.e. without the co-expression of said (poly)peptides.

In another embodiment, the present invention relates to a method, wherein said periplasmic protein is a resistance marker, a nutritional marker, a reporter protein, a transactivator of transcription of marker genes or reporter genes, or a protein binding to a target. As has been stated hereinabove in step (c), the functional yield is determined by screening or selecting for an increase in protein function. If the protein is a periplasmic resistance marker such as $\beta$-lactamase, or zeocin causing resistance to a certain antibiotic when functionally present in the periplasm, a selection is possible by culturing the host cells in the presence of said antibiotic.

Host cells expressing the marker in functional form will be selected for. If the protein is a periplasmic nutritional marker such as maltose-binding protein or an amino-acid-binding protein, a selection is possible by using auxotrophic host cells and by culturing the cells in the presence of maltose, or the amino acid, respectively. Host cells expressing the marker in functional from will be selected for. If the protein is a periplasmic reporter protein such as alkaline phosphatase, a screening is possible by culturing the host cells in the presence of the corresponding substrate resulting in a colour reaction. Host cells expressing the reporter protein in functional form will be selected for. If the protein is a secreted protein having enzymatic activity or binding to a target, a screening of the supernatant of individual cell cultures or of a collection of host cells on a plate can be performed by adding the appropriate substrate or target, respectively, to the medium and measuring or determining the amount of functional protein being secreted. It will be possible for a person of ordinary skill in the art, without undue burden, to identify and adapt existing screening or selection protocols, e.g. based on the various ELISA formats known, to arrive at protocols which are suitable for the indidual proteins and the corresponding function to be screened of selected for.

In a further preferred embodiment, said first nucleic acid sequence is or is derived from genomic DNA or mRNA of an organism, or cDNA.

Further preferred is a method, wherein said genomic DNA is randomly fragmented. Genomic DNA can be fragmented by use of restriction enzymes or DNA cleaving enzymes, chemical cleavage, mechanical shearing or sonification. These are standard procedures well known to anyone of ordinary skill in the art (Sambrook et al., 1989).

In a yet further preferred embodiment of the present invention, said first nucleic acid sequence comprises an at least partially randomized sequence. Such at least partially randomized sequences can be generated in various ways well known to the practitioner in the field, e.g. by random DNA syntheses using mixtures of mononucleotides or trinucleotides (Virnekäs et al., 1994). There are numerous examples of collections of nucleic acid sequences encoding random peptide or antibody libraries which could be used in accordance with the present invention.

In a further preferred embodiment, the present invention relates to a method, wherein (a) said first nucleic acid sequence is comprised in a vector which can be packaged in a filamentous phage particle, and (b) said periplasmic protein is a fusion protein of at least part of a filamentous phage coat protein and a further protein;

and wherein in the course of said expression a collection of filamentous phage particles displaying said further protein is produced from said collection of host cells.

The term "filamentous phage particles displaying said further protein" refers to particles prepared by the phage display method which has been developed and used extensively in the past 10 years. In said method, a foreign (poly)peptide or protein is genetically fused to a coat protein of a phage, in most cases of a filamentous phage such as M13, f1 of fd, whereby said phage displays said foreign (poly)peptide or protein at its surface. Many important aspects of phage display are summarized in various publications (e.g. Kay et al., 1996).

In one further embodiment of the present invention, the vector wherein said first nucleic acid sequence is comprised is a phage vector or a phagemid vector. In the latter case, a helper phage will be used to supply phage proteins not encoded on the phagemid vector.

In another embodiment of the present invention, the phage coat protein is the gVlp, gVlllp or preferably glllp.

In a preferred embodiment of the present invention, binding of the displayed protein to a cognate binding partner is screened or selected for. If the protein is an antibody, the cognate binding partner is the corresponding antigen (and vice versa). In the case of a receptor, the cognate binding partner is its ligand (and vice versa). The particular advantage of this embodiment of the method of the present invention is that rare events leading to an increase in functional yield can be selected for since the selected phage particles can be used for infection of host cells and can thus be amplified.

In yet another embodiment, said screening or selection is for activity of the displayed further protein.

If the activity is an enzymatic activity, the supernatant of individual host cell cultures can be used to assay for the enzymatic activity.

In a still further embodiment, said further protein comprises at least a domain of the immunoglobulin superfamily, and preferably of the immunoglobulin family. In the context of the present invention, the term immunoglobulin superfamily (IgSF) refers to a family of proteins which are characterized by having at least a domain with the immunoglobulin fold, said superfamiliy comprising the immunoglobulins or antibodies, and various other proteins such as T-cell receptors or integrins. in a most preferred embodiment, said further protein is an immunoglobulin fragment taken from the list of Fv, scFv, disulphide-linked Fv, and Fab fragments. In this context, the term "Fv" refers to a fragment comprising the VL (variable light) and VH (variable heavy) portions of the antibody molecule, a "single-chain Fv" is a fragment, in which the VL and VH chains are joined, in either a VL-VH, or VH-VL orientation, by a peptide linker. A "disulphide-linked Fv" is a fragment stabilized by an inter-domain disulphide bond. This is a structure which can be made by engineering into each chain a single cysteine residue, wherein said cysteine residues from two chains become linked through oxidation to form a disulphide. The term "Fab" refers to a complex comprising the VL-CL (variable and constant light) and VH-CH1 (variable and first constant heavy) portions of the antibody molecule.

In yet a further preferred embodiment, the invention relates to the method wherein said first and second nucleic acid are encoded on the same or on different vectors.

In a still further embodiment, the present invention relates to a method for identifying a (poly)peptide which increases the expression yield of a periplasmic protein in functional form in bacteria upon co-expression of said periplasmic protein and said (poly)peptide, comprising the steps of:

(a) identifying a nucleic acid sequence or a (poly)peptide coding sequence according to a method of the invention as outlined hereinabove, and (b) deducing a (poly)peptide therefrom.

The deduction of a (poly)peptide can be achieved by translating the (poly)peptide encoding sequence into an amino acid sequence. By comparing the deduced (poly) peptide sequence with published protein sequences, or by comparing the (poly)peptide coding sequence identified as described above with published nucleic acid sequences, larger (poly)peptides, or (poly)peptide coding sequences, respectively, can be deduced and identified in cases where said first nucleic acid sequence did not comprise the full-length nucleic acid coding sequence of a protein. In addition to the method described hereinabove, the (poly)peptide may be identified directly by known methods from the host cells screened or selected for. For example, said (poly)peptide may be expressed as a fusion with a detection or labelling tag. The tagged (poly)peptide may be isolated and identified by amino acid sequencing.

In a most preferred embodiment, the present invention relates to a method for increasing the expression of a periplasmic protein in functional form in a bacterial host cell, characterized by co-expressing said periplasmic protein and a (poly)peptide identified by a method according to the the present invention. Preferably, said bacterial host cells are *E. coli* cells.

In a further preferred embodiment, said periplasmic protein is not expressible, or in very low yields, in functional form when expressed under standard conditions, i.e. without the co-expression of said (poly)peptides.

In a yet further preferred embodiment, said periplasmic protein is a member of a collection of periplasmic proteins expressed in a collection of host cells. Several methods such as the phage display technology referred to hereinabove provide libraries of proteins for screening or selection procedures. However, the success of the procedures is limited by differences in expression yields of functional library members. For example, in the case antibody fragments, it is known that the expression yields of fragments in functional form vary to a large extent. A high percentage of fragments comprised in antibody fragment libraries derived from immunoglobulin repertoires is found not to be expressible, or in very low yield when expressed under standard conditions, i.e. without the co-expression of said (poly) peptides.

When expressing periplasmic proteins with yet unknown biological function, or a collection of periplasmic proteins for the identifcation or a member with a certain property (e.g. when expressing an antibody fragment library with the goal to identify a fragment which binds to a pre-defined target), the term "expression . . . in functional form" refers to structural features rather than to a defined biological function. In that context, a protein can be called "functional" when it folds into a three-dimensional arrangement representative for that kind of proteins. For example, when expressing a collection of antibody molecules of fragments thereof, a "expression . . . in functional form" is achieved when said molecules of fragments are expressed in a correctly folded form, the so-called immunoglobulin fold, since correct folding of an antibody binding site is a prerequisite for its function, i.e. the binding to a target.

In a further preferred embodiment, said (poly)peptide is the *E. coli* protein Skp or a homolog thereof.

In a further preferred embodiment, said (poly)peptide is the *E. coil* protein FkpA or a homolog thereof.

Proteins are termed homologous if the percentage of the sum of identical and/or similar residues exceeds a defined threshold. This threshold is commonly regarded by those skilled in the art as being exceeded when at least 15% of the amino acids in the aligned genes are identical, and at least a further 30% are similar. Similarity in that context refers to the physico-chemical properties of the amino acids, such as e.g. size, polarity, or charge.

Proteins which are homologous to Skp are known from organisms such as *Salmonella typhimurium* (Koski et al., 1990 ; Koski et al., 1989), *Yersinia enterocolitica* (Hirvas et al., 1991), *Yersinia pseudotuberculosis* (Vuorio et al., 1991), *Haemophilus influenzae* (Fleischmann et al., 1995) and *Pasteurella multocida* (Delamarche et al., 1995). Proteins which are homologous to FkpA are present e.g. in many pathogenic bacteria (Horne and Young, 1995). In *Legionella pneumophila* the corresponding protein showing PPl activity is called MipA.

In a yet further preferred embodiment, the invention relates to a method wherein said periplasmic protein is a fusion protein of at least part of a filamentous phage coat protein and a further protein.

Still further preferred is a method wherein said further protein comprises at least a domain of the immunoglobulin superfamily, and preferably of the immunoglobulin family.

Most preferably, the invention relates to a method wherein the further protein is an immunoglobulin fragment taken from the list of Fv, scFv, disulphide-linked Fv, and Fab fragment.

In yet a further preferred embodiment, the invention relates to the method wherein the nucleic acid sequence encoding said (poly)peptide, preferably Skp, FkpA, or a homolog of Skp or FkpA, and the gene encoding said periplasmic protein are encoded on the same or on different vectors, or wherein the nucleic acid sequence encoding the (poly)peptide, preferably Skp, FkpA, or a homolog of Skp or FkpA, is integrated in the genome of the bacterial host.

BRIEF DESCRIPTION OF THE DRAWINGS

FIG. 1. Selection scheme. A. Principle of selection. An *E. coli* genomic library is co-expressed with a scFv-fragment, fused to g3p. While the antibody is the same throughout, its folding yield varies depending on the co-expressed factor. This factor is not displayed on the phage, but expressed in the host cell producing the phage, which in the case of an useful factor leads to better "quality" scFv fragments displayed. Since the gene for the factor is encoded on the phage, its information becomes enriched by phage panning on antigen. B. Phagemid vector used for library construction.

FIG. 2. Analysis of phagemid pools after different panning rounds. For each round of phage proliferation, phagemids were prepared from cells harvested from overnight cultures. The phagemid pools were analyzed by restriction digest with NotI. M: PstI digested λ-DNA as molecular weight marker, lane 1 to 7: phagemids from infected cells after the panning round. lane 0: phagemids before the first panning round.

FIG. 3. Schematic representation of the 952 bp insert enriched by phage display and panning. Yaet is the product of an ORF of 810 aa of unknown function. It shows 66.2% similarity to amino acids of the protective surface antigen D15 of *Haemophilus influenzae* and those of other bacteria (see Example 1.3.). The gene IpxD codes for UDP-3-O-[3-hydroxymyristoyl]-glucosamine-N-acyltransferase. The only complete ORF found on this insert is the gene skp. Note that the Sau3AI fragment obtained is the smallest one which contains the full expression unit of Skp. SD, Shine-Dalgarno sequence; p, promoter region, predicted by neural network analysis (Reese, 1994).

FIG. 4. Antigen-binding ELISAs of phages grown with or without over-expressed Skp, displaying the scFv fragments 4-4-20 (Nieba et al., 1997), 4D5Flu (Jung and Plückthun, 1997), FITC-E2 (Vaughan et al., 1996; Krebber et al., 1997a) and ABPC48-CH22S (Proba et al., 1997; Proba et al.; 1998). Phages were purified by CsCl gradients as described in Example 1.2. Phages grown in the presence of over-expressed Skp reach higher antigen-binding ELISA signals compared to phages grown without over-expressed Skp. Inhibition with soluble antigen shows that binding is specific.

FIG. 5. Phage blot. Phage carrying g3p-fusion of the scFv fragments 4-4-20 (Nieba et al., 1997), 4D5Flu (Jung and Pluckthun, 1997), FITC-E2 (Vaughan et al., 1996; Krebber et al., 1997a), McPC603-H11 (Knappik and Plückthun, 1995), ABPC48-CH22S (Proba et al., 1997; Proba et al.; 1998) and AL214 were grown with or without over-expressed Skp. Phages were purified by CsCl gradients as described in Example 1.2. In the presence of over-expressed Skp, more fusion protein is incorporated into the phages than in the absence of Skp on the plasmid. Helper phage VCS M13 (Stratagene) was loaded as size reference for g3p wt.

FIG. 6. Crude extract ELISA. From E. coli JM83 expressing the soluble scFv fragments 4-4-20 (Nieba et al., 1997) and ABPC48-CH22S (Proba et a., 1997; Proba et al.; 1998) with or without over-expressed Skp crude extracts were prepared as described in Example 1.2. ScFv fragments produced in the presence of Skp give higher antigen binding ELISA signals than without skp on the plasmid. Inhibition with soluble antigen shows that binding is specific.

FIG. 7. Analysis of phagemid pools after different panning rounds. For each round of phage proliferation, phagemids were prepared from cells harvested from overnight cultures. The phagemid pools were analyzed by restriction digest with NotI. M: PstI digested λ-DNA as molecular weight marker, lane 1 to 7: phagemids from infected cells after the panning round. lane 0: phagemids before the first panning round.

FIG. 8. Schematic representations of the 1629 bp and 1987 inserts enriched by phage display and panning. YheO is a protein with strong similarity to H. influenzae Hl0575. FkpA is a peptidyl-prolyl cis-trans isomerase. SlyX is a protein with yet unknown function. SlyD is a peptidyi-prolyl cis-trans isomerase. YheP is a protein with yet unknown function.

FIG. 9. Antigen-binding ELISAs of phages grown with or without over-expressed Skp, FkpA, SlyX, FkpA+SlyX, and FkpA+Skp, displaying the scFv ABPC48- C(H22)S (Proba et al., 1997; Proba et al., 1998). Phages were purified by CsCl gradients as described in Example 1.2. Phages grown in the presence of over-expressed Skp reach higher antigen-binding ELISA signals compared to phages grown without over-expressed Skp. Inhibition with soluble antigen shows that binding is specific.

The examples illustrate the invention:

EXAMPLES

Example 1

Identification and application of Skp 1.1. Introduction

We have made use of the hypothesis, that g3p fusion-proteins might fold in the same environment and use the same machinery as periplasmically expressed proteins, in a search for cellular factors which might aid both the folding of periplasmic proteins and proteins displayed on phage. We have used a very poorly folding single-chain Fv fragment of the antibody 4-4-20 (Bedzyk et al., 1990), (Whitlow et al., 1995), specific for fluorescein, as a model system. Previous work (Nieba et al., 1997) showed that this scFv strongly aggregates in the bacterial periplasm, even though the same protein, once in the native state, is very soluble and stable. This indicates that not the final product limits the yield, but that the folding pathway branches off to aggregates. For this and similar cases, the folding yield is a kinetic and not a thermodynamic problem, and can thus potentially be helped by cellular factors.

We wished to identify such factors without any prejudice concerning whether they are membrane-bound, periplasmic, or even cytoplasmic proteins. We also wanted to be able to find any factors with might affect the total yield of the product without directly influencing folding. We therefore developed a selection system making use of phage display (FIG. 1A). The poorly folding scFv fragment was displayed as a fusion protein with g3p, and a library of E. coli proteins was co-expressed on the same phagemid. We reasoned that, if a particular E. coli cell produces a beneficial factor encoded on this phagemid, this cell will give rise to phages which outcompete the other phages, because a higher fraction of the phages will display correctly folded scFv. Thus, while the displayed scFv is genetically identical on all phages, this method selects for the effect of the additional factor encoded on the same phagemid, even though the factor itself is not displayed. This factor improves the "quality" of the scFv, namely the percentage of correctly folded molecules displayed on the phage, by acting on the host cell which produces the particular phage.

Using this strategy (FIG. 1A), a gene from E. coli was enriched, coding for the periplasmic protein Skp, which had been suspected previously to have a role in folding or transport of outer membrane proteins (Chen & Henning, 1996).

1.2. Experimental Protocols

Construction of Genomic Library

A NotI site was inserted in the phage display vector pAK100 (Krebber et al., 1997) at position 5656. A polylinker was inserted as an oligonucleotide cassette into this NotI site. The gel-purified SfiI fragment encoding the scFv fragment of the anti-fluorescein antibody 4-4-20 (Bedzyk et al., 1990) was ligated in this vector pHB100, yielding the plasmid pHB102. Genomic DNA of E. coli JM83 was isolated with Qiagen-tip 100G according to the manufacturer's protocol. The genomic DNA was partially digested with Sau3AI and applied to a 1% agarose gel. The range of 1 kb to 6 kb length was cut out, and the genomic DNA eluted with GenElute™ agarose spin columns (Supelco), phenol/chloroform extracted and ethanol precipitated. After ligation of the E. coli library in the BglII site of the polylinker of pHB102, the ligation mixture was precipitated with n-butanol and electroporated into E. coli XL1-Blue (Stratagene). After plating on 2xYT in 530 cm² dishes (Nunc) and overnight incubation at 37° C., the colonies were washed off the plates with 5 ml 2xYT, the $OD_{550}$ was determined and the cells stored at −80° C. after addition of glycerol to 10% final concentration.

Phage Panning

A 10 ml culture of 2xYT, containing 15 μg/ml tetracycline (tet), containing 0.1 ml salt mixture (0.86 M NaCl, 0.25 M KCl, 1 M $MgCl_2$) was inoculated to an $OD_{550}$ of 0.1 with E. coli harboring the genomic library. After 1 h incubation at 37° C. chloramphenicol (cam) was added to a concentration of 30 μg/ml, and the cells were grown to an $OD_{550}$ of 0.5. Then $10^{12}$ pfu of helper phage VCS M13 (Stratagene) was added and incubated for 15 min without agitation at 37 ° C., followed by addition of 50 ml 2xYT medium containing 30 μg/ml cam, 15 μg/ml tet, 0.5 ml salt mixture, 0.1 mM isopropyl-β-D-thiogalactoside (IPTG), and then shaken for 2 h at 37° C. After addition of 30 μg/ml kanamycin (kan) the cultures were grown overnight at 37° C. The cells were harvested and the phagemid DNA isolated (QIAprep spin kit, Qiagen). The phages from the culture supernatant were precipitated by incubation for 30 min with ¼ volume PEG/NaCl solution (17% PEG 6000, 3.3 M NaCl, 1 mM EDTA) on ice, and the pellets were redissolved in 2 ml PBS (8 mM $Na_2HPO_4$, 1.8 mM $KH_2PO_4$, 137 mM NaCl, 3 mM KCl, pH 7.4 (Sambrook et al., 1989)). Immunotubes (Nunc) were coated with 20 µg/ml fluorescein-isothiocyanate coupled to bovine serum albumin (FITC-BSA) in PBS overnight at 4° C. and blocked with 5% skimmed milk in PBST (PBS containing 0.05% Tween-20) for at least 1 h at room temperature. Five hundred µl of the phage solution was filled to a final volume of 5 ml with 2% skimmed milk in PBST and applied to the tubes for 2 h at room temperature. The tubes were washed 20 times with PBST and 2 times with PBS. Bound phages were eluted with 1 ml 0.1 M glycine/HCl pH 2.2 for 10 min. The eluate was neutralized immediately with 60 µl 2 M Tris and the phages (typically $10^4$–$10^6$ cfu) were used for re-infection.

Phage Purification and ELISA

Phage ELISAs were carried out to assay the amount of functionally displayed scFv on M13 phages. Single colonies were grown at 37° C. overnight in 5 ml 2xYT medium containing 30 µg/ml cam and 15 µg/ml tet. Ten ml of 2xYT medium containing 30 µg/ml cam, 15 µg/ml tet, 0.4% glucose and 0.1 ml salt mixture was inoculated with the overnight culture to give an $OD_{550}$ of 0.1. At an $OD_{550}$ of 0.3 to 0.5, $10^{12}$ cfu VCS helper phage (Stratagene) were added. After 15 min, 50 ml 2xYT medium containing 30 µg/ml cam, 15 µg/ml tet, 0.5 ml salt mixture and 0.1 mM IPTG was added. After 2 h at 37° C., kan was added to a final concentration of 30 µg/ml and the cells were grown overnight. The phages were precipitated from the culture supernatant by incubating for 30 min with ¼ volume PEG/NaCl solution as above on ice, and the pellets were redissolved in 1 ml PBS. After addition of 1.6 g of CsCl, the volume was adjusted to 4 ml with PBS. The CsCl solution was transferred into a ½×1½ in. polyallomer tube and centrifuged at 100,000 rpm for 4 hr in a TLN-100 rotor (Beckman Intruments) at 4° C. After centrifugation the phage band was removed as described (Smith & Scott, 1990). The phages were transferred to ½×2 in. polycarbonate tubes, which were filled with PBS to 3 ml. After centrifugation at 50,000 rpm for 1 hr in a TLA-100.3 rotor at 4° C., the pelleted phages were redissolved in 3 ml PBS. After an additional centrifugation at 50,000 rpm for 1 hr in a TLA-100.3 rotor at 4° C., the phages were dissolved in PBS. The concentration of phage particles was quantified spectrophotometrically (Day, 1969). ELISA plates were coated with FITC-BSA in PBS, for anti-levan antibodies with 10 µg/ml levan (polyfructose, Sigma) in PBS at 4° C. overnight. The plates were blocked for 1 h at room temperature. A defined number of purified phages (measured by OD) (Day, 1969) were mixed with 2% skimmed milk in PBST in the absence or presence of 10 µM fluorescein or 0.05% levan and applied to the blocked ELISA plates and incubated for 1 h at room temperature. Detection was as above, using an anti-M13 antibody conjugated with horseradish peroxidase (Pharmacia).

Phage Blots

For phage blots $10^{11}$ phages were applied to a reducing 11% SDS-PAGE, and blotted on nitrocellulose membranes. Detection was carried out with the monoclonal antibody 10C3 (Tesar et al., 1995), which recognizes the C-terminal half of g3p (1:50.000 in TBST (25 mM Tris/HCl pH 7.5, 150 mM NaCl, 0.05% Tween-20) containing 2% milk), for 60 min at RT, followed by incubation with a polyclonal anti-mouse-peroxidase conjugate (Pierce) (1:5000 in TBST/2% milk, 45 min RT) and using the ECL-kit (Amersham).

Crude Extract ELISA

Fifty ml of LB medium containing 30 µg/ml cam were inoculated with a single colony of *E. coli* JM83, harboring a plasmid encoding the respective scFv fragment. The cultures were grown at 24° C. to an $OD_{550}$ of 0.5 and induced with 1 mM IPTG. After overnight induction at 24° C. the cells were harvested and resuspended in 4 ml PBS. Whole cell extracts were prepared by French Press lysis at 10,000 psi and 1 ml of the crude extract was centrifuged in an Eppendorf tube for 30 min at 50.000 rpm in a TLA-100.3 rotor (Beckman Instruments) at 4° C. After centrifugation the supernatants containing the soluble material were normalized to an $OD_{550}$ of 20 in 1 ml. ELISA plates were coated and blocked as described above for phage ELISAs. A defined amount of crude extract was mixed with 2% skimmed milk in PBST in the absence or presence of 10 µM fluorescein or 0.05% levan and applied to the blocked ELISA plates and incubated for 1 h at room temperature. The signal was detected with an anti-myc-tag antibody (Munro & Pelham, 1986) and an anti-mouse antibody conjugated with horseradish peroxidase and soluble BM blue POD-substrate (Boehringer-Mannheim), and after stopping the reaction with 0.1 M HCl, the signals were read at 405 nm.

Protein Purification

The anti-phosphorylcholine scFv McPC603-H11 (Knappik & Plückthun, 1995) was purified using PC-Sepharose affinity chromatography (Skerra & Pl ückthun, 1988) in the presence or absence of co-expressed Skp. The concentration and yield was estimated photometrically using a calculated extinction coefficient (Gill & von Hippel, 1989).

1.3. Identification of Skp

We used a phagemid displaying the poorly folding scFv fragment of the anti-fluorescein antibody 4-4-20 (Bedzyk et al., 1990; Nieba et al., 1997) as the recipient for an *E. coli* genomic library. *E. coli* DNA was size-fractionated from 1 to 6 kb and ligated into a polylinker placed between the colE1 origin of replication and the chloramphenicol (cam) resistance gene of a phagemid (FIG. 1B) developed for phage display (Krebber et al., 1997). Thus, *E. coli* genes, regulated under their own promoters, are over-expressed on the phagemid, primarily through an effect of vector copy number. A library size of $5 \times 10^4$ clones ensured that each piece of the *E. coli* genome should be represented, provided it led to viable clones. Seven panning rounds on BSA-fluorescein were carried out (FIG. 1A), and after each round the phagemid DNA was cut with the restriction enzyme NotI to detect the accumulation of any inserts. It can be seen in FIG. 2 that a band of about 990 bp accumulates throughout the panning. Four of 8 single colonies analyzed after the seventh round carried this insert, which was sequenced and identified to only contain the complete gene for the periplasmic protein Skp (Holck & Kleppe, 1988), from 272 bases upstream of the start codon to 199 bases downstream of the stop codon (FIG. 3). Four bases after the stop codon of skp is the start codon of IpxD (firA), leading to a truncated peptide of the 65 N-terminal amino acids of this protein. One-hundred and twenty-five base pairs upstream of the start codon of the skp gene lies the stop codon of an open reading frame, which codes for an 810 aa protein with unknown function. A homology search showed 66.2% similarity to the protective surface antigen D15 of *Haemophilus influenzae* (Swiss-Prot: P46024), and surface proteins of *Pasteurolla multocida* (TREMBL: Q51930) and *Neisseria gonorrhoeae* (TREMBL: P95359).

1.4. Effects of Skp Co-expression on Phage Display

To determine how and why Skp gets enriched, we first characterized the phages produced in the absence or presence of co-expressed Skp. For this purpose, we cloned a variety of different scFv fragments in the phagemid with and without skp. The phage titer was indistinguishable within experimental error, demonstrating that Skp is not selected because it would lead to the production of more phages.

However, the antigen binding phage ELISA signal from the same number of purified phage particles is higher, proving that the Skp over-expression increases the number of functional antibody molecules on the phage (FIG. 4). This effect is seen with all four antibodies tested, albeit to different degrees.

We then determined whether the total amount of fusion protein per phage is also increased by the over-expression of Skp. For this purpose we analyzed the amount of full-length fusion protein on purified phage particles in the presence or absence of skp on the phagemid by Western blot, using the monoclonal antibody 10C3 (Tesar et al., 1995) (FIG. 5). For the scFv 4-4-20, the co-expression of Skp dramatically increased the presence of fusion protein presented on the phage. Since the same amount of purified phages was loaded on the gel, Skp must facilitate the incorporation of functional fusion protein into the phage, which is also reflected by the antigen-binding ELISA (see above). It can be seen that Skp has this effect on all of the six antibodies tested, albeit to a different extent and to different final level of incorporation. Since the fusion protein is still only a minor species when compared to g3p wt (encoded by the helper phage), we cannot reliably determine a decrease of g3p wt, but most likely, the scFv-g3p fusion protein takes the place of g3p wt more often in the presence of over-expressed Skp.

1.5. Effects of Skp Co-expression on Soluble Protein Expression

We then determined the effect of Skp on the production of several of the scFv fragments in soluble form using the non-suppressor strain JM83. Using antigen-binding ELISA (FIG. 6) it can be seen that the amount of soluble scFv was dramatically increased in the presence of co-expressed Skp. To demonstrate that this is also reflected in the yield of purified protein, the scFv fragment of the anti-phosphorylcholine binding antibody McPC603-H11 (Knappik & Plückthun, 1995) was tested. Co-expression of Skp increased the amount of protein, purified by affinity-chromatography on phosphorylcholine by about a factor of 4.

The results of FIG. 4 and FIG. 5 suggest that the more an scFv fragment tends to aggregate in the periplasm of *E. coli*, the stronger is the influence of Skp in the phage ELISA. For the scFv fragment of FITC-E2 (Vaughan et al., 1996; Krebber et al., 1997a), which folds very well und shows little insoluble material when expressed in the periplasm, we observed a reduced influence of Skp in the phage ELISA, compared to the poorly folding scFv 4-4-20 (Nieba et al., 1997) and ABPC48-C(H22)S (Proba et al., 1997; Proba et al., 1998). The engineered Flu4D5 (Jung & Plückthun, 1997), with improved properties compared to 4-4-20, is intermediate. This shows that the better an scFv is functionally expressed and the less aggregation-prone it is, the less is the influence of Skp, suggesting that Skp supports the correct folding of poorly expressed scFv fragments and its fusion proteins.

Example 2
Identification and Application of FkpA
2.1. Experimental Protocols
Construction of Genomic Library The gel-purified Sfil fragment encoding the scFv fragment of the anti-levan antibody ABPC-C(H22)S (Proba et al., 1997; Proba et al., 1998) was ligated in the vector pHB100 (Bothmann and Plückthun, 1998), yielding the plasmid pHB121. Genomic DNA of *E. coli* RC354c (Chen and Henning, 1996) was isolated with Nucleobond AXG100 cartridge according to the manufacturer's protocol (Macherey-Nagel). The genomic DNA was partially digested with Sau3Al and applied to a 1% agarose gel. The range of 1 kb to 6 kb length was cut out, and the genomic DNA eluted with GenEluteTM agarose spin columns (Supelco), phenol/chloroform extracted and ethanol precipitated. After ligation of the *E. coli* library in the Bglll site of the polylinker of pHB121, the ligation mixture was precipitated with n-butanol and electroporated into *E. coli* XL1-Blue (Stratagene). After plating on 2xYT in 530 cm$^2$ dishes (Nunc) and overnight incubation at 37° C., the colonies were washed off the plates with 5 ml 2xYT, the OD550 was determined and the cells stored at −80° C. after addition of glycerol to 50% final concentration.

Phage Panning

Phage panning was done as described in Example 1. Instead using FITC-BSA, the immunotubes (Nunc) were coated with 10 μg/ml levan (polyfructose, Sigma) in PBS overnight at 4° C.

Phage Purification and ELISA

Phage purification and ELISA was done exactly as described in Example 1.

2.2. Phage Selection and Identification of Coexpressed Factor

We used a phagemid displaying the poorly folding scFv fragment of the anti-levan antibody ABPC48-C(H22)S as the recipient for an *E. coli* genomic library. *E. coli* RC354c-DNA (skp-deficient strain) was size-fractionated from 1 to 6 kb and ligated into the polylinker of plasmid pHB121. Thus, *E. coli* genes, regulated under their own promoters, are over-expressed on the phagemid, primarily through an effect of vector copy number. A library size of 6.4×10$^5$ clones ensured that each piece of the *E. coli* genome should be represented, provided it led to viable clones.

Seven panning rounds on levan were carried out, and after each round the phagemid DNA was cut with the restriction enzyme Notl to detect the accumulation of any inserts. It can be seen in FIG. 7 that two bands of about 1.7 kb and 2.0 kb accumulate throughout the panning. Fourteen of 17 single colonies analyzed after the seventh round carried the 1.7 kb insert, 3 the 2.0 kb insert. Both inserts were sequenced and the 1.7 kb band contains an insert of 1629 bp length, the 2.0 kb band an insert of 1987 bp length (FIG. 8). Both inserts contain the same two complete genes coding for the periplasmic protein FkpA (Horne and Young, 1995; Missiakas et al., 1996) and the protein SlyX with unknown function. Both inserts start 218 bp upstream of the stop codon of fkpA. Therefore both inserts code for the first 21 aa of the gene yheO, which codes for a protein with strong similarity to *Haemophilus influenzae* HI0575. The 1629 bp insert ends 159 bp downstream of the stop codon of slyX, whereas the 1987 bp insert ends 528 bp downstream of the stop codon of slyX. Both inserts code for the C-terminal part of SlyD (Roof et al., 1994; Roof et al., 1997; Hottenrott et al., 1997). The 1987 bp insert codes also for the first 117 aa of YheP, an protein with unknown function. To examine, which of the two complete genes is responsible for enrichment, fkpa and slyX were PCR-amplified and precisely recloned separately as well as in combination at the same position in the vector pHB102 (see Example 1).

2.3. Characterization of the Influence of FkpA and SlyX on Phage Display

To determine how and why FkpA and SlyX get enriched, we characterized the phages produced in the absence and presence of co-expressed FkpA and SlyX. The antigen binding phage ELISA (FIG. 9) shows, that over-expression of FkpA increases the number of functional antibody molecules on the phage, compared to no over-expression or over-expression of Skp. In contrast, the over-expression of SlyX has no effect on the number of functional antibody molecules on the phage.

REFERENCES

Aasland, R., Coleman, J., Holck, A. L., Smith, C. L., Raetz, C. R. and Kleppe, K. 1988. Identity of the 17-kilodalton protein, a DNA-binding protein from *Escherichia coli*, and the firA gene product. *J. Bacteriol.* 170:5916–5918.

Bardwell, J. C. 1994. Building bridges: disulphide bond formation in the cell. *Mol. Microbiol.* 14:199–205.

Bedzyk, W. D., Weidner, K. M., Denzin, L. K., Johnson, L. S., Hardman, K. D., Pantoliano, M. W., Asel, E. D. and Voss, E. W., Jr. 1990. Immunological and structural characterization of a high affinity anti-fluorescein single-chain antibody. *J. Biol. Chem.* 265:18615–18620.

Bothmann, H. and Plückthun, A. 1998. Selection for a periplasmic factor im proving phage display and funktional periplasmic expression. *Nature Biotech.* 16:376–380.

Buchner, J. 1996. Supervising the fold: functional principles of molecular chaperones. *FASEB J.* 10:10–19.

Chen, R. and Henning, U. 1996. A periplasmic protein (Skp) of *Escherichia coli* selectively binds a class of outer membrane proteins. *Mol. Microbiol.* 19:1287–1294.

Danese, P. N. and Silhavy, T. J. 1997. The $\sigma^E$ and the Cpx signal transduction systems control the synthesis of periplasmic protein-folding enzymes in *Eschelichia coli*. *Genes and Development* 11:1183–1193.

Day, L. A. 1969. Conformations of single-stranded DNA and coat protein in fd bacteriophage as revealed by ultraviolet absorption spectroscopy. *J. Mol. Biol.* 39:265–277.

Delamarche, C., Manoha, F., Behar, G., Houlgatte, R., Hellman, U. and Wroblewski, H. 1995. Characterization of the *Pasteurella multocida* skp and firA genes. *Gene* 161:39–43.

Dunn, I. S. 1996. Phage display of proteins. *Curr. Opin. Biotechnol.* 7:547–553.

Fleischmann, R. D., Adams, M. D., White, O., Clayton, R. A., Kirkness, E. F., Kerlavage, A. R., Bult, C. J., Tomb, J. F., Dougherty, B. A., Merrick, J. M. and et al. 1995. Whole-genome random sequencing and assembly of *Haemophilus influenzae* Rd. *Science* 269:496–512.

Geyer, R., Galanos, C., Westphal, O. and Golecki, J. R. 1979. A lipopolysaccharide-binding cell-surface protein from *Salmonella minnesota*. Isolation, partial characterization and occurrence in different Enterobacteriaceae. *Eur. J. Biochem.* 98:27–38.

Gill, S. C. and von Hippel, P. H. 1989. Calculation of protein extinction coefficients from amino acid sequence data. *Anal. Biochem.* 182:319–326.

Hirvas, L., Coleman, J., Koski, P. and Vaara, M. 1990. Bacterial 'histone-like protein I' (HLP-I) is an outer membrane constituent? *FEBS Lett.* 262:123–126.

Hirvas, L., Koski, P. and Vaara, M. 1991. The ompH gene of *Yersinia enterocolitica*: cloning, sequencing, expression, and comparison with known enterobacterial ompH sequences. *J. Bacteriol.* 173:1223–1229.

Holck, A. and Kleppe, K. 1988. Cloning and sequencing of the gene for the DNA-binding 17K protein of *Escherichia coli*. *Gene* 67:117–124.

Holck, A., Lossius, I., Aasland, R. and Kleppe, K. 1987. Purification and characterization of the 17 K protein, a DNA-binding protein from *Escherichia coli*. *Biochim. Biophys.* Acta 914:49–54.

Horne, S. M. and Young, K. D. 1995. *Escherichia coli* and other species of Enterobacteriaceae encode a protein similar to the family of Mip-like FK506-binding proteins. *Arch. Microbiol.* 163:357–365.

Hottenrott, S., Schumann, T., Plückthun, A., Fischer, G. and Rahfeld, J. U. 1997. The *Escherichia coli* SlyD is a metal ion-regulated peptidyl-prolyl cis/trans-isomerase. *J. Chem. Biol.* 272:15697–15701.

Jung, S. and Plückthun, A. 1997. Improving in vivo folding and stability of a single-chain Fv antibody by loop grafting. *Protein Eng.* 10:959–966.

Knappik, A., Krebber, C. and Plückthun, A. 1993. The effect of folding cataysts on the in vivo folding process of different antibody fragments expressed in *Escherichia coli*. *Bio/Technology* 11: 77–83.

Knappik, A. and Plückthun, A. 1995. Engineered turns of a recombinant antibody improve its in vivo folding. *Protein Eng.* 8:81–089.

Kay, B., Winter, J. and McCafferty, J. (ed.) 1996. Phage display of peptides and proteins: a laboratory manual Koski, P., Hirvas, L. and Vaara, M. 1990. Complete sequence of the ompH gene encoding the 16-kDa cationic outer membrane protein of *Salmonella typhimurium*. *Gene* 88:117–120.

Koski, P., Rhen, M., Kantele, J. and Vaara, M. 1989. Isolation, cloning, and primary structure of a cationic 16-kDa outer membrane protein of *Salmonella typhimurium*. *J. Biol. Chem.* 264:18973–18980.

Krebber, A., Bornhauser, S., Burmester, J., Honegger, A., Willuda, J., Bosshard, H. R. and Pleckthun, A. 1997. Reliable cloning of functional antibody variable domains from hybridomas and spleen cell repertoires employing a reengineered phage display system. *J. Immunol. Meth.* 201:35–55.

Krebber, C., Spada, S., Desplancq, D., Krebber, A., Ge, L. and Plückthun, A. 1997a. Selectively-infective phage (SIP): A mechanistic dissection of a novel in vivo selection for protein-ligand interactions. *J. Mol. Biol.* 268:607–618.

Makrides, S. C. 1996. Strategies for achieving high-level expression of genes in *Escherichia coli*. *Microbiol. Rev.* 60:512–538.

Martin, J. and Harti, F. U. 1997. Chaperone-assisted protein folding. *Curr. Opin. Struct. Biol.* 7:41–52.

McGregor, D. 1996. Selection of proteins and peptides from libraries displayed on filamentous bacteriophage. *Mol. Biotechnol.* 6:155–62.

Missiakas, D. and Raina, S. 1997. Protein misfolding in the cell envelope of *Escherichia coli*: new signaling pathways. *Trends Biochem. Sci.* 22:59–63.

Missiakas, D., Betton, J. M. and Raina, S. 1996. New components of protein folding in extracytoplasmic compartments of *Escherichia coli* SurA, FkpA and Skp/OmpH. *Mol. Microbiol.* 21:871–884.

Munro, S. and Pelham, H. R. 1986. An Hsp70-like protein in the ER: Identity with the 78 kd glucose-regulated protein and immunoglobulin heavy chain binding protein. *Cell* 46: 291–300.

Nieba, L., Honegger, A., Krebber, C. and Plückthun, A. 1997. Disrupting the hydrophobic patches at the antibody variable/constant interface: improved in vivo folding and physical characterization of an engineered scFv fragment. *Protein Eng.* 10:435–444.

Proba, K., Honegger, A. and Plückthun, A. 1997. A natural antibody missing a cysteine in VH: consequences for thermodynamic stability and folding. *J. Mol. Biol.* 265:161–172.

Proba, K., Worn, A., Honegger, A. and Plückthun, A. 1998. Antibody fragments without disulphide bonds, made by molecular evolution. *J. Mol. Biol.* 275: 245–253.

Raetz, C. R. H. (1996). *Escherichia coli and Salmonella* (Curtiss III, R., Ingraham, J. L., Lin, E. C. C., Low, K. B., Magasanik, B., Reznikoff, W. S., Riley, M., Schaechter, M., Umbarger, H. E. and Neidhardt, F. C.) pp. 1035–1063, ASM Press, Washington, D.C.

Reese, M. G. (1994) Diploma Thesis, German Cancer Research Center, Heidelberg.

Roof, W. D., Horne, S. M., Young, K. D. and Young, R. 1994. slyD, a host gene required for fX174 lysis, is related to the FK506-binding protein family of peptidyl-prolyl cis-trans-isomerases. *J. Biol. Chem.* 269:2902–2910.

Roof, W. D., Fang, H. Q., Young, K. D., Sun, J. and Young, R. 1997. Mutational analysis of slyD, an *Escherichia coli* gene encoding a protein of the FKBP immunophilin family. *Mol. Microbiol.* 25:1031–1046.

Sambrook, J., Fritsch, E. F. and Maniatis, T. (1989) *Molecular Cloning: A laboratory manual*, Cold Spring Harbor Laboratory Press, Cold Spring Harbor, USA.

Skerra, A. and Plückthun, A. 1988. Assembly of a functional immunoglobulin Fv fragment in *Escherichia coli*. *Science* 240:1038–1041.

Smith, G. P. and Scott, J. K. 1993. Libraries of peptides and proteins displayed on filamentous phage. *Methods. Enzymol.* 217:228–257.

Söderlind, E., Simonsson Lagerkvist, A. C., Duenas, M., Malmborg, A.-C., Ayala, M., Danielsson, L. and Borrebaeck, C. A. K. 1993. Chaperonin assisted phage display of antibody fragments on filamentous bacteriophages. *BioTechnology* 11:503–506.

Szabo, A., Langer, T., Schröder, H., Flanagan, J., Bukau, B. and Hartl, F. U. 1994. The ATP hydrolysis-dependent reaction cycle of the *Escherichia coli* Hsp70 system—Dnak, DnaJ, and GrpE. *Proc. Natl. Acad. Sci. U.S.A.* 91: 10345–10349.

Tesar, M., Beckmann, C., Roettgen, P., Haase, B., Faude, U. and Timmis, K. N. 1995. Monoclonal antibody against pIII of filamentous phage: An immunological tool to study pIII fusion protein expression in phage display systems. *Immunotechnology* 1:53–64.

Thome, B. M. and Müller, M. 1991. Skp is a periplasmic *Escherichia coli* protein requiring SecA and SecY for export. *Mol. Microbiol.* 5:2815–2821.

Thome, B. M., Hoffschulte, H. K., Schiltz, E. and Müller, M. 1990. A protein with sequence identity to Skp (FirA) supports protein translocation into plasma membrane vesicles of *Escherichia coli*. *FEBS Lett.* 269:113–116.

Vaughan, T. J., Williams, A. J., Pritchard, K., Osborn, J. K., Pope, A. R., Earnshaw, J. C., McCafferty, J., Hodits, R. A., Wilton, J. and Johnson, K. S. 1996. Human antibodies with sub-nanomolar affinities isolated from a large non-immunized phage display library. *Nature Biotechnology* 14:309–314.

Virnekäs, B., Ge, L., Plückthun, A., Schneider, K. C., Wellnhofer, G. and Moroney, S. E. 1994. Trinucleotide phosphoramidites: ideal reagents for the synthesis of mixed oligonucleotides for random mutagenesis. *Nucleic Acids Res.* 22: 5600–5607.

Vuorio, R., Hirvas, L., Raybourne, R. B., Yu, D. T. and Vaara, M. 1991. The nucleotide and deduced amino acid sequence of the cationic 19 kDa outer membrane protein OmpH of *Yersinia pseudotuberculosis*. *Biochim. Biophys. Acta* 1129:124–126.

Wall, J. G. and Plückthun, A. 1995. Effects of over-expressing folding modulators on the in vivo folding of heterologous proteins in *Escherichia coli*. *Curr. Opin. Biotechnol.* 6:507–516.

Whitlow, M., Howard, A. J., Wood, J. F., Voss, E. W., Jr. and Hardman, K. D. 1995. 1.85 Å structure of anti-fluorescein 4-4-20 Fab. *Protein Eng.* 8:749–761.

---

---

What is claimed is:

1. A method for increasing the expression of a heterologous periplasmic protein in functional form in a bacterial host cell, characterized by co-expressing said periplasmic protein and a (poly)peptide identified by:

(a) providing a collection of host cells wherein each cell comprises
  (i) a first nucleic acid sequence out of a collection of nucleic acid sequences, and
  (ii) a second nucleic acid sequence encoding said heterologous periplasmic protein;

(b) causing or allowing expression of
  (i) (poly)peptides expressible from said collection of nucleic acid sequences, and
  (ii) said heterologous periplasmic protein expressible from said second nucleic acid sequence;

(c) screening or selecting for a host cell expressing said heterologous periplasmic protein with increased functional yield, wherein the polypeptide encoded by said first nucleic acid sequence and expressed in the screened or selected host cell enhances the folding of said periplasmic protein;

(d) optionally, repeating step (c) one or more times;

(e) obtaining said first nucleic acid sequence contained in said host cell; and (f) deducing a (poly)peptide sequence therefrom.

2. The method of claim 1, wherein said periplasmic protein is a member of a collection of periplasmic proteins expressed in a collection of host cells.

3. The method of claim 1 wherein said (poly)peptide is the *E. coli* protein Skp or a homolog thereof.

4. The method of claim 1 wherein said (poly)peptide is the *E. coli* protein FkpA or a homolog thereof.

5. The method of claim 1 wherein said periplasmic protein is a fusion protein of at least part of a filamentous phage coat protein and a further protein.

6. The method of claim 1 wherein said further protein comprises at least a domain of the immunoglobulin superfamily.

7. The method of claim 6, in the further protein is an immunoglobulin fragment selected from the group consisting of Fv, scFv, disulphide-linked Fv, and Fab fragment.

8. The method of claim 6, wherein said further protein comprises at least a domain of an immunoglobulin.

9. The method of claim 1, wherein said first nucleic acid sequence is comprised in a vector which can be packaged in a filamentous phage particle.

10. The method of claim 9, wherein said periplasmic protein is expressed as a fusion protein with at least part of a filamentous phage coat protein on the surface of a filamentous phage particle.

11. A method for increasing the expression of a periplasmic protein in functional form in a bacterial host cell, characterized by co-expressing said periplasmic protein and a (poly)peptide identified by:

(a) providing a collection of host cells wherein each cell comprises (i) a first nucleic acid sequence out of a collection of nucleic acid sequences, and (ii) a second nucleic acid sequence encoding said periplasmic protein;

(b) causing or allowing expression of (i) (poly)peptides expressible from said collection of nucleic acid sequences, and (ii) said periplasmic protein expressible from said second nucleic acid sequence;

(c) screening or selecting for a host cell expressing said periplasmic protein with increased functional yield, wherein the polypeptide encoded by said first nucleic acid sequence and expressed in the screened or selected host cell enhances the folding of said periplasmic protein, and wherein said periplasmic protein is selected from the group consisting of a resistance marker, a nutritional marker, a reporter protein, a transactivator of transcription of marker genes or reporter genes, and a protein capable of binding to a target;

(d) optionally, repeating step (c) one or more times;

(e) obtaining said first nucleic acid sequence contained in said host cell; and (f) deducing a (poly)peptide sequence therefrom.

12. A method according to claim 11, wherein said protein capable of binding to a target is selected from the group consisting of $F_v$, scFv, disulphide-linked $F_v$ and $F_{ab}$.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Pro Phe
  1
```